(12) United States Patent
Hassard et al.

(10) Patent No.: US 7,372,038 B2
(45) Date of Patent: May 13, 2008

(54) ANALYSIS OF TEMPERATURE-DEPENDENT MOLECULAR CONFIGURATIONS

(75) Inventors: John Hassard, London (GB); Anthony Edward George Cass, London (FR)

(73) Assignee: Deltadot Limited, London (GB)

( * ) Notice: Subject to any disclaimer, the term of this patent is extended or adjusted under 35 U.S.C. 154(b) by 130 days.

(21) Appl. No.: 10/493,402

(22) PCT Filed: Oct. 3, 2002

(86) PCT No.: PCT/GB02/04484

§ 371 (c)(1),
(2), (4) Date: Oct. 26, 2004

(87) PCT Pub. No.: WO03/036302

PCT Pub. Date: May 1, 2003

(65) Prior Publication Data

US 2005/0054081 A1    Mar. 10, 2005

(30) Foreign Application Priority Data

Oct. 23, 2001 (GB) ................................. 0125436.6

(51) Int. Cl.
*G01J 1/42* (2006.01)
(52) U.S. Cl. .................... 250/372; 250/341.1
(58) Field of Classification Search ............ 250/341.1, 250/458.1, 372; 422/67
See application file for complete search history.

(56) References Cited

U.S. PATENT DOCUMENTS

| 5,255,976 | A | 10/1993 | Connelly | |
|---|---|---|---|---|
| 5,442,175 | A | 8/1995 | Dawson | |
| 6,036,920 | A * | 3/2000 | Pantoliano et al. | ............ 422/67 |
| 6,214,293 | B1 * | 4/2001 | Pantoliano et al. | ............ 422/67 |
| 6,948,843 | B2 * | 9/2005 | Laugharn et al. | ............ 366/127 |

FOREIGN PATENT DOCUMENTS

| WO | WO 97/42500 | 11/1997 |
|---|---|---|
| WO | WO 99/24050 | 5/1999 |
| WO | WO 99/46590 | 9/1999 |

OTHER PUBLICATIONS

Search Report for GB01/25436.6 dated May 30, 2002.
International Search Report for PCT/GB02/04484 mailed Jan. 23, 2003.
"Deadly Conformations-Protein Misfolding in Prion Disease," Horwich et al., *Cell*, vol. 89, pp. 499-510 (1997).

(Continued)

*Primary Examiner*—Dave Porta
*Assistant Examiner*—Marcus H Taningco
(74) *Attorney, Agent, or Firm*—Schwartz Cooper Chartered

(57) ABSTRACT

An apparatus and method for analysing temperature-dependent molecular configurations such as folding comprises a multi-channel flow-through chip (12) along which molecules to be analysed pass. A temperature gradient is maintained along the length of the chip. As molecules pass along the channels they fold or unfold, in response to the changing temperature. These changing molecular configurations are investigated by simultaneously measuring the extent to which the molecules absorb UV light, and the extent to which they fluoresce. The absorption and fluorescence information is supplied to a computer system (26) for real-time analysis.

51 Claims, 2 Drawing Sheets

OTHER PUBLICATIONS

"Applications of Three- and Four-Dimensional Heteronuclear NMR Spectroscopy to Protein Structure Determination," Clore et al., *Progress in NMR Spectroscopy*, vol. 23, pp. 43-92 (1991).

"BCH 5887 Protein Structure and Stability," Blaber et al., *Protein Structure and Stability Web Course Tutorial*, Florida State University (1995).

* cited by examiner

ANALYSIS OF TEMPERATURE-DEPENDENT MOLECULAR CONFIGURATIONS

CROSS REFERENCE TO RELATED APPLICATION

This Application is a U.S. National filing under § 371 of International Application No. PCT/GB02/04484, with an international filing date of 3 Oct. 2002, now pending, claiming priority from Great Britain Application No. GB01/25436.6, with a filing date of 23 Oct. 2001, now pending, and herein incorporated by reference.

TECHNICAL FIELD

The present invention relates generally to the analysis of temperature-dependent molecular configurations, and particularly although not exclusively to the folding of proteins, and to the binding of proteins to other molecules.

BACKGROUND OF THE INVENTION

Proteins are made up of a string of sub-units called amino acids, the sequence of which is known as the primary structure of the protein. This first level of organisation of the protein is directed by the gene sequence encoding the protein, wherein a sequence of three nucleic acids (a codon) in the gene specifies the nature of the amino acid at any particular position. In addition to the primary structure, most proteins also exhibit a higher level of structural organisation. It is this three dimensional, or tertiary, structure, which allows the protein to function in its biological role. Many proteins in the cell exist as aggregates of two or more folded proteins, or sub-units. This level of organisation is referred to as the quaternary structure of a protein.

Typically, proteins are made up of a number of folded domains, i.e. compact regions of folded structure. Several varieties of domains exist, including α-helices, β-sheets and β-turns.

A folded protein is held in its secondary or tertiary structure by several types of bonds. These include electrostatic interactions, which occur between the oppositely charged side chains of the amino acids making up the primary structure; hydrogen bonds between amino acids; weak interactions between uncharged groups (known as van der Waals interactions): and disulphide bonds between cysteine amino acid residues. Unfolding a protein by reversing these interactions is known as denaturing the protein, back to its primary structure. This may be achieved by placing the protein in a high temperature environment, or in SDS solution.

The folding of a protein to its final, functional conformation is one of the last steps in protein production. It is a vital step in a complex process, and any error in the process can induce massive physiological problems. For example, there is strong evidence to suggest that Bovine Spongiform Encephalopathy (BSE) stems from a mis-folded protein (Horwich et al Cell 89 499-510 (1997)). An understanding of protein folding and stability will provide a clearer insight into the causes of disease, and therefore will allow the development of better treatments or preventative measures for disease.

There exist a number of techniques to study proteins. These include X-ray crystallography ((Blundell et al Protein Crystallography London: Academic press (1976)); NMR (Clore et al Progress in NMR Spectroscopy 23 43-92 (1991)); differential scanning calirometry (Blaber et al protein structure and Stability Florida State University (1995)); and unnatural amino acid engineering (Mendel et al Science 256 (5065) 1798-1802 (1992)).

X-ray crystallography is a preferred method for determining the three dimensional structure of proteins. However, this technique has the fundamental problem that it can only be employed when the proteins are crystallised, and this is not always easy or even possible. This puts constraints on the ability to study conformational changes in the protein, changes in the folding in response to changes in environment, or interaction with other factors.

Florescence and absorption by certain optically active amino acids in a protein have also been used to monitor conformational changes in protein and to measure protein concentration (Chen et al Biochemistry 37 9976-9982 (1998)). These amino acids contain an indole chromophore whose transitional geometry is responsible for the optical activity of the amino acid (Callis et al Chemical Physics Letters 244 53-58 (1995); Fender et al Chemical Physics Letters 262 343-348 (1996) and Fender et al Chemical Physics Letters 239 31-37 (1995)). The main amino acids contributing to this are tryptophan and tyrosine, while phenylalanine and the disulphide bond between cysteine residues also show some fluorescence.

The problem encountered with all of the above mentioned techniques is that they are not capable of real-time protein folding analysis. This imposes significant constraints on protein folding and stability analysis, and therefore also on the use of proteins in the diagnosis and prevention and/or treatment of disease. Furthermore, current systems often reveal little about the relationship between the dynamics of the folding and the static conformational information available.

The present invention will be useful in any method where it is desirable to analyse the folding and/or stability of a protein, and/or the interaction of a protein with biological factors including ligands, receptors, sugars, hormones, nucleic acids and therapeutics agents. Other long chain or macromolecules may also be studied, as long as they are able to fold or otherwise change their physical configuration in response to a temperature change.

SUMMARY OF THE INVENTION

According to the present invention there is provided apparatus for analysing temperature-dependent molecular configurations, comprising:
  (a) a multi-lane chip having a plurality of channels extending along a length thereof, each channel being arranged for the passage of molecules to be analysed, and
  (b) heating elements associated with the chip for creating a temperature profile along the channels, thereby exposing molecules passing along the channels to corresponding temperature variations.

According to a further aspect of the present invention there is provided a method of analysing temperature-dependent molecular configurations, comprising:
  (a) defining a temperature profile along the length of a channel;
  (b) passing molecules to be analysed along the channel;
  (c) detecting an optical characteristic of the molecules as they pass along the channel; and
  (d) analysing the detected optical characteristic as a function of temperature.

To analyse the folding of a protein using the present invention, the protein is passed along a temperature gradient as described above. A decrease in temperature with passage of the protein will typically enable it to fold and adopt its secondary, tertiary or quaternary structure. In contrast, an increase in temperature along the path of the protein will typically cause the protein to be denatured, and unfold. As folding or unfolding occurs, the fluorescence emitted and light absorbed by the protein are measured, and used to generate a series of signals illustrative of the folding pattern. The signals (also referred to as the detected optical characteristics) produced will indicate the position of amino acids important in folding, and the sequence of folding events which result in the final structure.

The range of the temperature across the gradient will depend upon the nature of the protein being analysed, and may be adjusted according to the type of protein, and/or to the degree of folding or unfolding which is desired. Typically, the temperature range will be in the region of 20° C. to 200° C. The exact range for any particular molecule may be readily determined using techniques available in the art.

The invention as described in the above paragraphs will be useful in monitoring the quality of proteins produced recombinantly, particularly in terms of their ability to fold correctly and therefore function properly, and their stability. For example, the signals generated during the folding of recombinant proteins (or those produced in any other way by the hand of man) can be compared to those generated by a native protein of the same type, which preferably is known to be biologically active. In this way, proteins which do not share substantially the same signal output as the native protein may be discarded, and correctly folded proteins may be identified. Similarly, proteins which have been designed to differ from the native protein in terms of structure or stability may be identified by comparative techniques using the invention.

In the context of the present invention, a "native" protein or other biological factor or macromolecule is one which is found naturally in vivo i.e. in the human or animal body, in plants or other life forms.

In addition, the interaction of a protein with biological factors and/or other proteins may be analysed. By folding or unfolding a protein in the presence of a factor or protein with which it interacts, the sites critical to the interaction may be identified. This is achieved by passing the protein/protein or biological factor/protein complex along a temperature gradient, and monitoring the fluorescence emitted and light absorbed as the protein folds or unfolds. The signals generated may be compared to those generated by the same protein in the absence of the biological factor or other protein. Comparison of the data indicates the amino acids and folded domains important to interaction, and the temperature at which the complex breaks down.

This aspect will be particularly useful in the design of biological factors, such as therapeutic agents, with the aim of reproducing, enhancing or inhibiting the interaction. In particular, once the protein and/or biological factor domains important to interaction have been established, this information can be used to design new biological factors. The interaction of these with the protein, and their effect on its folding or stability can be tested using the invention. Preferably, the signals generated by the protein and native biological factor complex can be compared with those generated by the protein and/or candidate biological factor, to determine whether the interaction is the same, and if not, or how it differs.

This aspect of the invention is particularly useful in the production of therapeutic agents. Thus, candidate therapeutic agents not having the desired interaction can be identified by comparison of signal patterns generated with optimum agents or biological factors, and can be discarded.

The present invention will also be useful in identifying variants of proteins. A variant protein is typically one which differs from the "wild type" or reference protein in its primary structure, and may as a result have impaired biological function and/or may serve as a marker for disease. The wild type, or reference, protein is the functional, biologically active version.

Variations in the primary sequence may arise due to divergence in the gene sequence encoding the protein. Such divergent sites are known as polymorphisms, and are manifested as restriction fragment length polymorphisms, variable number of tandem repeats, hypervariable regions, minisatellites, di- or multi-nucleotide repeats, insertion elements and nucleotide deletions, additions or substitutions. A single nucleotide polymorphism (SNP) is a variation in sequence at a site occupied by a single nucleotide residue. Single nucleotide polymorphisms arise from the substitution, deletion or insertion of a nucleotide residue at a polymorphic site. Single nucleotide polymorphisms may result in corresponding changes to the amino acid sequence. For example, substitution of a nucleotide residue may change the codon, resulting in an amino acid change. Similarly, the deletion or insertion of three consecutive bases in the nucleic acid sequence may result in the insertion or deletion of an amino acid residue.

As a result of the change in the primary sequence, a variant protein may have a different folding pattern, or stability, compared to the wild type protein, or may show different interaction with biological factors. Proteins may be compared to a wild type protein in terms of their folding pattern, stability or interaction with biological factors by comparing the signals generated using the present invention. In this way, a protein may be identified as a variant or a wild type.

In addition, the invention may be used to detect SNPs in a protein. Any change in amino acid sequence at a particular position in a protein may be detected by comparing the signals generated by the amino acid at the position of the wild type sequence with the signal generated by the amino acid in that position in the protein to be analysed. Polymorphisms other than SNPs which cause amino acid changes may be detected in this way.

The invention may also be used in the correlation of polymorphisms with disease. For example, a protein from a diseased individual may be compared with the same protein from a normal individual, and differences in the signals generated may be used as markers for polymorphisms in the protein, which are associated with disease. This aspect of the invention may be used in diagnosing an individual as having, or being susceptible to disease. By determining the phenotype of an individual in this way, the efficacy of any treatment can be assessed.

BRIEF DESCRIPTION OF THE DRAWINGS

The invention may be carried into practice in a number of ways and one specific embodiment will now be described, by way of example, with reference to the accompanying drawings, in which.

DETAILED DESCRIPTION OF THE INVENTION

Figure 1:
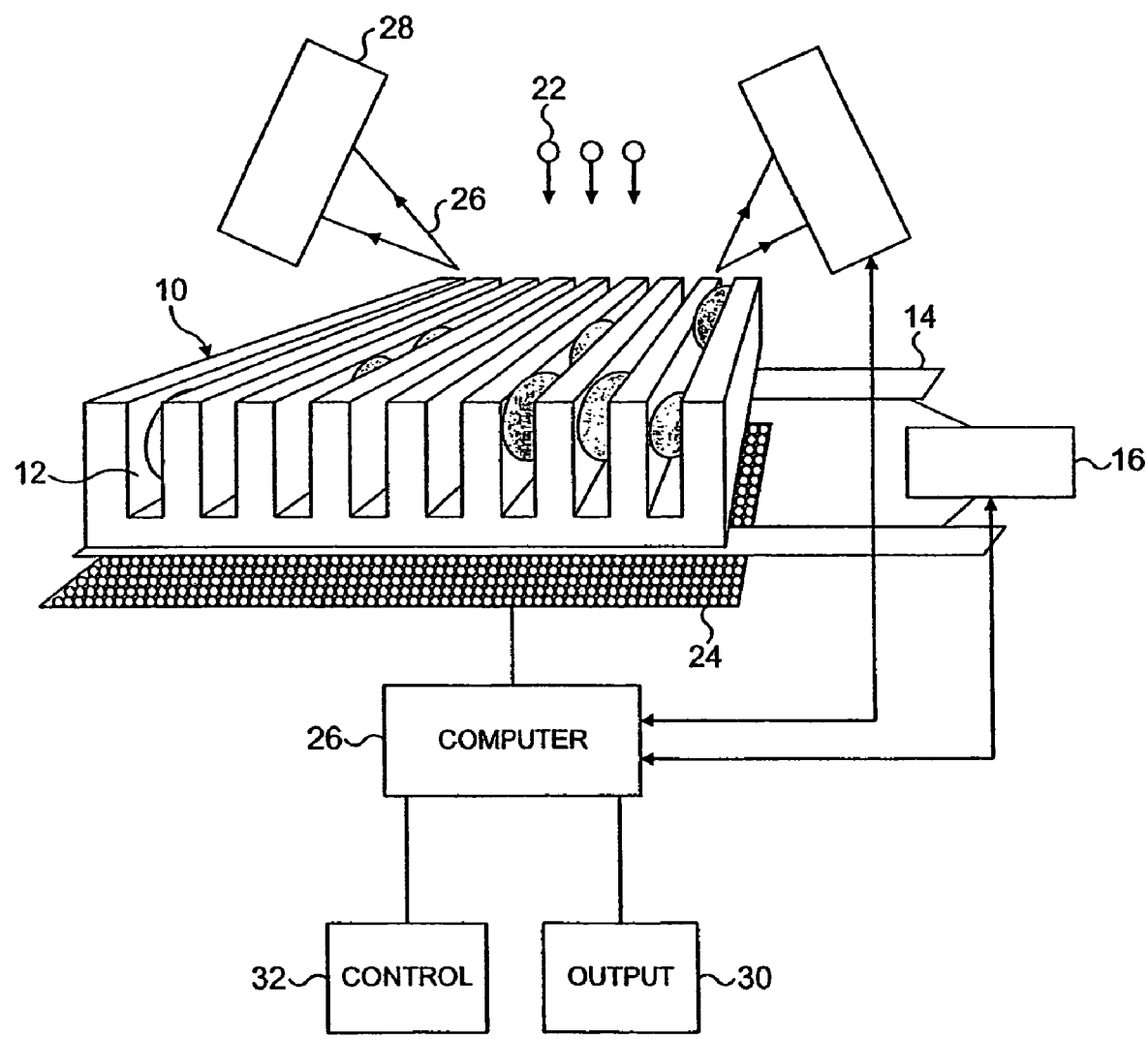
FIG. 1 schematically illustrates and apparatus for analysing molecular folders according to an embodiment of the present invention.

The heart of the apparatus shown in FIG. 1 is a multi-lane chip 10, the lanes being defined by a plurality of narrow, parallel-sided open-topped channels 12. The width of each channel may anything between a fraction of a micrometer to hundreds of micrometers, with the depth between a fraction of a micrometer to thousands of micrometers. In the preferred embodiment, the channels are about 50 micrometers wide and about 200 micrometers deep. The channels could also be defined by (closed) microcapillaries within the body of the chip.

The chip may be manufactured from polydimethylsiloxane (PDMS), but other stable, non-reactive, temperature-resistant material could also be used. The chip is of the "flow-through" type, in which a buffer containing the molecules to be analysed is continuously supplied via lead-in lines (not shown) to one end of the channels. The buffer and the molecules then passes along the channels and out the other end. The chip 10 is preferably angled so that the molecules and buffer pass along the channels simply under the force of gravity, but pumped or other pressurised systems could also be envisaged. It would also be possible to use electrokinetic means to transport the molecules.

Located beneath the channels 12, and at right angles thereto, are a series of thermal heating strips 14 (only two of which are shown in FIG. 1, for clarity). The temperatures of these heating strips may be varied by means of a thermal control 16, thereby introducing a temperature gradient along the length of the channels. The thermal control 16 is able to alter the temperature gradient according to the type of analysis to be undertaken. Sometimes, for example, the temperature may be monotonically increasing along the length of the channels (in the direction of molecular movement), whereas in others it may be monotonically decreasing. For some types of analysis, multi-valued gradients may be useful—for example with low temperatures being maintained at the ends of the channels and a high temperature in the middle.

Figure 2:
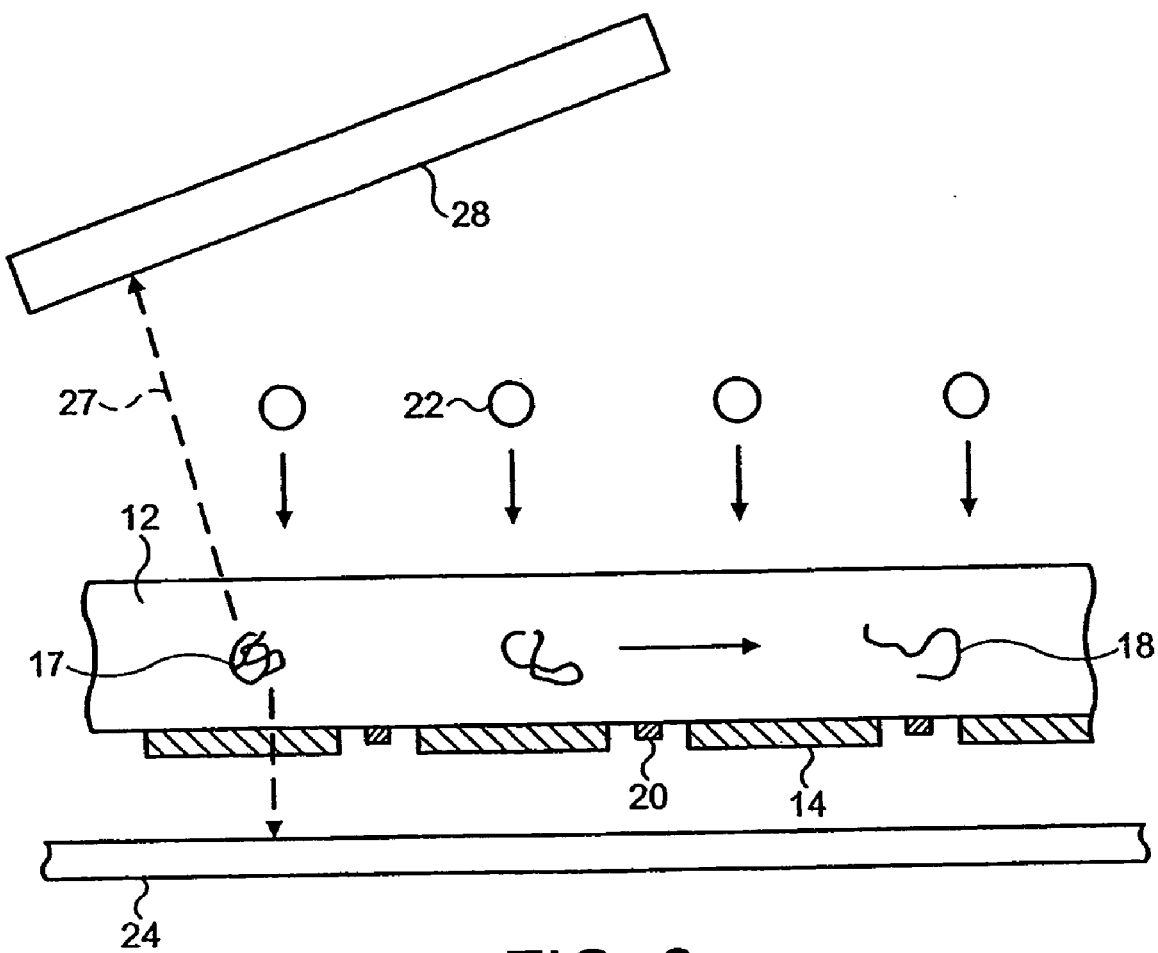
FIG. 2 is a schematic longitudinal section through the apparatus of FIG. 1.

As the molecules move along the channels, their physical configurations change as they are exposed to differing temperature regimes. As is best shown in FIG. 2, in a rising temperature regime, for example, a protein originally in a folded state 17 will gradually unfold as indicated at 18. Multi-valued temperature gradients, mentioned above, may be useful in studies which seek to compare the unfolding sequence of a particular molecule with the folding sequence. At the most basic level, a user may simply wish to know whether, once a molecule has been unfolded by increasing its temperature, it will naturally fold up again when the temperature is reduced.

An array of temperature detectors such as thermocouples 20 constantly monitors the temperature of each channel, as a function of the distance (z) along the channel. This allows a one to one mapping to be maintained so that once a particular molecule's position (z) is known within the channel, its temperature is then uniquely determined. So, in order to study how the configuration of a particular molecule varies with temperature, we no longer need to control very closely the temperature of a bulk sample of the molecule: instead, we simply need to watch how the molecule changes its configuration as a function of z.

As the molecules travel along the channels they are exposed to UV illumination, from above, emanating from a UV source 22. As the UV light passes through the molecules, it is selectively absorbed, with the amount of absorption varying according to the physical configuration of the molecule. Typically, an unfolded molecule 18 will absorb less UV light than will a folder molecule 17. The UV light passes through the PDMS chip 10 (which is substantially UV-transparent) and is detected by an underlying optical detector array 24. This may be for example a photodiode array (PDA) or a charge coupled device (CCD). The output of the detector array 24 is fed to a computer system for storage and analysis. Since the fast, real-time analysis of multiple channels is extremely processor-intensive, the computer system 26 may include hardware-based data-capture and analysis. In the preferred approach, a data-capture unit (not shown) feeds raw information to a plurality of digital signal processors (DSPs) controlled by a field programmable gate array (FPGA). Of course, other data-capture and analysis systems may be contemplated. Preferably, though, the computer system 26 is capable of carrying out analysis in real time (i.e. as the molecules being analysed are moving along the channels).

The UV illumination from source 22 causes the molecules to fluoresce, and this fluorescence 26 is detected by means of one or more hybrid photo diodes (HPDs) 28, located above the chip. Each HPD is essentially a multi-channel photo-multiplier tube array, which is capable of detecting the fluorescence from a large number of molecules at once and determining, for each molecule, both the channel within which it sits and also its position (z) within the channel. z is measured sufficiently precisely to define the temperature narrowly enough to observe threshold effects and time-resolved processes. The output of the HPD, which is thus essentially a fluorescence map taken across the length and width of the chip, is passed for analysis to the computer system 26. Similar considerations apply to data-capture and analysis as were discussed above with reference to the detector array 24.

Scattered light may be detected, instead of fluorescence. Rather than using an HPD, the fluorescence or scattered light may be detected by means of a multi-anode photo-multiplier tube.

In one embodiment (not shown) dual wavelength absorption and/or fluorescence/scattering may be measured. This allows investigation of attraction and/or bonding between two molecules to be studied. For example, in a study of the bonding of sugars to proteins, the absorption/fluorescence/scattered light may be detected at wavelengths tuned to both the protein and the sugar. Where such an approach is used, dual-wavelength IR sources are provided, along with suitable dual-wavelength detectors (not shown).

It is believed (although so far as the applicant is aware no comprehensive research has yet been done on this) that UV absorption measurements are at least partly indicative of the static properties of the molecules, whereas fluorescent measurements are at least partly indicative of dynamic properties. By making both measurements simultaneously on the same molecule, as a function of temperature, substantial additional information can be derived, over and above either measurement taken on its own.

Some of the channels within the chip may be used as controls, and may be fed with known types of protein or other molecules. By comparing the outputs of the control channels and the test channels, the user can investigate the way in which small changes between different proteins or other molecules may affect its folding characteristics.

The precise analysis to be carried out by the computer system 26 will of course depend upon the particular investigation being undertaken. Typically, however, users will be interested in the cross-correlation between some combination of fluorescence and absorption measurements within a control channel and similar measurements simultaneously being carried out in one or more test channels. Other possible calculations of interest may be the cross correlation, within a single channel, between the fluorescence and the absorption measurements, as well as auto-correlation calculations. The calculations may be carried out for a fixed thermal gradient, as defined by the thermal control 16, and also for a range of different thermal gradients. All of this is done under control of the computer system 26.

A calculation output 30, such as a graphics screen or a printer, provides the user with analytical output on the analysis being undertaken. Alternatively, or in addition, a control 32 may be provided which automatically controls the experimental apparatus in dependence upon the real-time outputs. For example, the control 32 might automatically change the UV illumination, alter the thermal control, or change the detection characteristics of the hybrid photo diode 28 or the detector array 24. Also, the control 32 may provide for the automated collection of particular molecular samples of interest, in dependence upon the real-time results of the analysis. One way of doing this is shown in FIG. 3.

Figure 3:
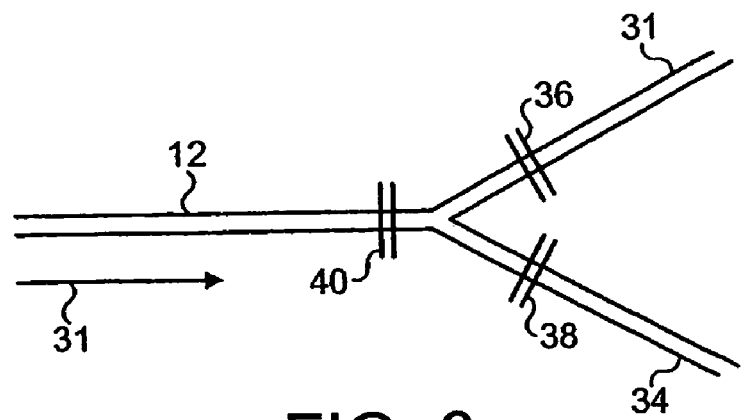
FIG. 3 shows, again schematically, how molecules travelling along a particular channel may be switched out under computer control.

FIG. 3 shows that the end of one of the channels 12 (in the direction of flow 31 of the molecules), is bifurcated into two output channels 32, 34. Electrodes 36,38 at the entrance of the channels 32,34 allow a potential difference to be applied to each of the channel entrances, thereby allowing molecular samples to be selectively switched into either of the two channels. When a particular molecule to be collected reaches the bifurcation, a high voltage is applied between the electrode 38 and an electrode 40 at the end of the main channel, thereby diverting the sample into the channel 34. Once the sample has been collected, the high voltage is switched from the electrode 38 to the electrode 36, thereby causing all subsequent molecules to pass down into the channel 32. The collected sample in the channel 34 may then be further analysed, for example by means of a mass-spectrometer or by means of MALDI-TOF (Matrix Assisted Laser Desorption Ionisation-Time of Flight).

The switching of the voltage between the electrodes 36,38 may be effected by the control 32, which is itself actuated by the results of the computer analysis carried out by the computer system 26. The control 32 may also, if desired, be activated at least partly in dependence upon the raw absorption or fluorescence information or characteristics defining the state of the apparatus such as the type of thermal gradient being applied, the time of change of any thermal gradient, the intensity of the UV illumination, the time that illumination was switched on so on. Generally, the control 32 may operate in dependence upon any variable of the apparatus itself, the raw data being collected, or the analysed data. In the particular embodiment of FIG. 3, the control 32 automatically acts to collect samples of particular molecules which appear to be of some particular interest (that is, they meet some predefined or dynamic criteria of interest based upon the real-time results of the analysis carried out by the computer system 26).

The system of the preferred embodiment is expected to find particular application in the analysis of proteins. The range of possible analyses that can be carried out is evidently extremely broad, but they include: investigations into the thermal stability of proteins; analysis of the mechanism of thermal unfolding; evaluation of the effects of mutations on thermal stability (such as SNP's in nucleic acids by which the proteins are expressed); and evaluations of the effects of environmental conditions on molecular stability. In addition, the system may be used to investigate how other proteins bind to molecules, and how this is affected by temperature changes. In particular, the system may be used to investigate how changes to a protein's thermal stability affect the capability of small molecules to bind.

A typical analysis that could be carried out with the described apparatus relates to the effect of different dosages of a particular drug. For example, very high dosage regimes may cause undesirable protein changes to occur within the patient. In order to investigate this, protein samples would be obtained from a range of patients who are being treated with different amounts of the drug, and these proteins would be compared, channel by channel, with a control channel which contains the corresponding "normal" protein. Such an analysis allows very rapid decisions to be made on the efficacy of particular drug treatments and dosing regimes.

The invention claimed is:

1. An apparatus for analysing temperature-dependent molecular configurations, comprising:
   (a) a multi-lane chip having a plurality of channels extending along a length thereof, each channel being arranged for the passage of molecules to be analysed; and,
   (b) heating elements associated with the chip for creating a temperature profile along the channels, thereby exposing molecules passing along the channels to corresponding temperature variations.

2. An apparatus as claimed in claim 1 further including temperature sensors spaced along the length of each channel for measuring the temperature profile.

3. An apparatus as claimed in claim 1 further including a detector measuring an optical characteristic of the molecules as the molecules pass along the channels.

4. An apparatus as claimed in claim 3 in which the optical characteristic is fluorescence, and in which the detector detects the molecular fluorescing in response to UV illumination as the molecules pass along the channels.

5. An apparatus as claimed in claim 4 in which the detector is one of either a hybrid photodiode or a multi-anode photo-multiplier tube.

6. An apparatus as claimed in claim 3 in which the optical characteristics is UV absorption and in which the detector detects a reduction in transmitted UV illumination, as a result of molecular absorption.

7. An apparatus as claimed in claim 6 in which the detector is one of either a charge-coupled device or a photodiode array.

8. An apparatus as claimed in claim 1 further including first and second detectors for simultaneously measuring respective first and second optical characteristics of the molecules as the molecules pass along the channels.

9. An apparatus as claimed in claim 8 in which the first detector detects the molecules fluorescing in response to UV illumination and in which the second detector detects a reduction in transmitted UV illumination as a result of molecular absorption.

10. An apparatus as claimed in claim 3 further including a UV source for creating UV illumination.

11. An apparatus as claimed in claim 1 in which the chip is orientated so that the molecules pass along the channels under the influence of gravity.

12. An apparatus as claimed in claim 1 in which the molecules are either pumped along the channels or urged along by an electric force.

13. An apparatus as claimed in claim 3 further including computer analysis means for receiving an output of the detector(s) and arranged to analyse the output(s) as a function of molecular temperature.

14. An apparatus as claimed in claim 13 further including an apparatus control arranged automatically to control operation of the apparatus in dependence upon an output of the computer analysis means.

15. An apparatus as claimed in claim 14 in which the apparatus control actuates a molecule collection mechanism for automatically collecting a sample of selected molecules from a channel.

16. An apparatus as claimed in claim 15 in which the molecule collection mechanism includes voltage switching means for switching the sample into a side branch of the channel.

17. An apparatus as claimed in claim 13 in which the computer analysis means calculates a cross-correlation between output(s) indicative of known molecules in a control channel and output(s) indicative of molecules for analysis in another channel.

18. An apparatus as claimed in claim 1 in which the heating elements are controllable to create a user-defined temperature profile along the channels.

19. An apparatus as claimed in claim 18 in which the heating elements are controlled to create a monotonic increasing or decreasing temperature profile along the channels.

20. An apparatus as claimed in claim 18 in which the heating elements are controlled to create a multi-valued temperature profile along the channels.

21. A method of analysing temperature-dependent molecular configurations, comprising the steps of:
    (a) defining a temperature profile along the length of a channel;
    (b) passing molecules to be analysed along the channel;
    (c) detecting an optical characteristic of the molecules as the molecules pass along the channel; and,
    (d) analysing the detected optical characteristic as a function of temperature.

22. A method as claimed in claim 21 in which the optical characteristic is analysed as a function of position along the channel, each position uniquely defining a temperature at that position in accordance with the profile.

23. A method as claimed in claim 21 in which the optical characteristic is molecular fluorescence.

24. A method as claimed in claim 21 in which the optical characteristic is the molecules' capacity for UV absorption.

25. A method as claimed in claim 21 further including the step of simultaneously detecting first and second optical characteristics.

26. A method as claimed in claim 25 in which the first optical characteristic is molecular fluorescence and in which the second optical characteristic is the molecules' capacity for UV absorption.

27. A method as claimed in claim 21 further including the step of automatically collecting selected molecules in dependence upon a result of analysing the detected optical characteristic as a function of temperature.

28. A method as claimed in claim 21 further including the steps of: passing control molecules along a control channel adjacent to the channel carrying molecules to be analysed;
    detecting a corresponding optical characteristic(s) of the control molecules; and,
    comparing the optical characteristic(s) of the molecules to be analysed with the corresponding optical characteristic(s).

29. A method as claimed in claim 28 further including the step of calculating a cross-correlation between the characteristic(s) and the corresponding characteristic(s).

30. A method as claimed in claim 21 in which the molecules to be analysed are macro-molecules.

31. A method as claimed in claim 21 in which the molecules to be analysed are proteins.

32. A method as claimed in claim 21 comprising the step of analysing molecular folding as a function of temperature.

33. A method as claimed in claim 21 comprising analysing molecular bonding as a function of temperature.

34. A method as claimed in claim 21 comprising the step of analysing molecular stability as a function of temperature.

35. A method as claimed in claim 21 further including the step of using the detected optical characteristic(s) to determine either a folding pattern or a sequence of folding events of the molecule.

36. A method as claimed in claim 21 further including the step of using the detected optical characteristic(s) to identify residues of the molecule involved in folding.

37. A method according to claim 36 wherein the molecule is a protein and the residues are amino acids.

38. A method as claimed in claim 21 wherein the molecule to be analysed is either a protein/biological factor or protein/protein complex.

39. A method according to claim 38 wherein the biological factor is a sugar, hormone, ligand, receptor or nucleic acid.

40. A method as claimed in claim 38 further including the step of determining the domains necessary for interaction of a protein with a biological factor or protein.

41. A method as claimed in claim 40 further including the step of designing therapeutic agents therefrom.

42. A method as claimed in claim 41 further including the steps of:
    passing the native protein/biological factor or protein/protein complex along a control channel adjacent to the channel carrying the protein/candidate therapeutic agent complex to be analysed;
    detecting a corresponding optical characteristic(s) of the native protein/biological factor or protein/protein complex; and,
    comparing the optical characteristic(s) of the protein/candidate therapeutic agent complex to be analysed with the corresponding optical characteristic(s).

43. A method as claimed in claim 28 further including the step of analysing a recombinant protein, wherein the control molecule is the native protein and the molecule to be analysed is the recombinant protein.

44. A method as claimed in claim 21 further including the steps of:
    comparing the detected optical characteristic(s) of a wild type protein with the detected optical characteristic(s) of a candidate protein; and,
    identifying a polymorphism in a protein.

45. A method as claimed in claim 44 wherein the polymorphism is a SNP.

46. A method as claimed in claim 21 further including the steps of:
    comparing the detected optical characteristic(s) of the protein with those of a wild type or a variant protein; and,
    determining whether a protein is either a wild type or a variant.

47. A method as claimed in claim 21 further including the steps of:
- comparing the detected optical characteristic(s) of a molecule from a non-diseased individual with detected optical characteristic(s) of the corresponding molecule from a diseased individual; and,
- identifying polymorphisms associated with disease.

48. A method as claimed in claim 21 further including the steps of:
- comparing the detected optical characteristic(s) of a molecule from an individual with the detected optical characteristic(s) of the form of the molecule known to be associated with a disease; and,
- diagnosing an individual as having, or being susceptible to, disease.

49. A method as claimed in claim 48 wherein the molecule to be analysed is from a sample removed from a human or animal body.

50. An apparatus as claimed in claim 2 further including first and second detectors measuring respective first and second optical characteristics of the molecules.

51. An apparatus as claimed in claim 50 in which the first and second detectors are receptive to light of first and second wavelengths, respectively.

* * * * *